United States Patent [19]

Otsuka et al.

[11] Patent Number: 5,085,995

[45] Date of Patent: Feb. 4, 1992

[54] METHOD FOR PRODUCING SAFFRON STIGMA-LIKE TISSUE AND METHOD FOR PRODUCING USEFUL COMPONENTS FROM SAFFRON STIGMA-LIKE TISSUE

[75] Inventors: Masako Otsuka, Souka; Hiroshi Saimoto, Misato; Yumiko Murata, Ageo; Masao Kawashima, Warabi, all of Japan

[73] Assignee: Somar Corporation, Tokyo, Japan

[21] Appl. No.: 399,037

[22] Filed: Aug. 28, 1989

[51] Int. Cl.$^5$ .............................. C12N 5/04; C12P 1/00
[52] U.S. Cl. .............................. 435/240.45; 435/240.4; 435/41
[58] Field of Search ........... 435/240.4, 240.45, 240.48, 435/240.54, 147, 41

[56] References Cited

U.S. PATENT DOCUMENTS 4,672,035 6/1987 Davidonis ..................... 435/240.4

FOREIGN PATENT DOCUMENTS 0261862 3/1988 European Pat. Off. .

OTHER PUBLICATIONS

Hashimoto, et al. (1987), Agric. Biol. Chem. 51(10): 2769.
Patent Abstracts of Japan, p. 124, C659; and JP-A-1,218,584) (Somar Corp.), 08-31-1989.
Chemical Abstracts, vol. 112, 1990, p. 621, Abstract No. 6135a, Columbus, Ohio, US, and JP-A-01 43198 (Q.P. Corp.),02-15-1989.
Sano et al. (1987), Plant Cell, Tissue and Organ Culture 11: 159-166.
Hori et al. (1988), Plant Tissue Culture Letters 5: 72-77.
Saito (1988), Z. Naturforsch Sect. C. Bio. Sci. 43(11-12): 862-870.
Himeno et al. (1988), Plant Science 58:93-101.
Himeno et al. (1987), Agric. Biol. Chem. 51:2395-2400.
Agric. Biol. Chem., 51(9) 2395-2400, 1987, Synthesis of Crocin, Picrocrocin and Safranal by Saffron Stigma-like Structures Proliferated in Vitro, Himeno et al.
Plant Tissue Culture Letters, 5(2) 72-77 (1988), Induction of Callus from Pistils of Crocus Sativus L. and Production of Color Compounds in the Callus, Hori et al.
Planta Med. 1988, 54(4) 375-6, Formation of Stigma-like Structures and Pigment in Culture Tissues of Crocus sativus, Koyama et al.
1. Planta Medica, vol. 54, No. 4, 1988, pp. 375-376; A. Koyama et al.
Patent Abstracts of Japan, p. 123 C 659, & JP-A-1 218 583 (Somar Corp.) 08-31-1989.
Patent Abstracts of Japan, p. 124, C 659, & JP-A-1 218 584 (Somar Corp.) 08-31-1989.
Agricultural and Biological Chemistry, vol. 51, No. 9, pp. 2395-2400, H. Himeno et al.
Chemical Abstracts, vol. 112, 1990, p. 621, Abstract No. 6135a, Columbus, Ohio, U.S., & JP-A-01 43 198 (Q.P. Corp.) 02-15-1989.
Biological Abstracts, vol. 85, No. 6, 1988, p. Ab-837, Abstract No. 60932, Philadelphia, U.S., Koyama et al.
Patent Abstracts of Japan, p. 61 C 564, JP-A-63 240 782 (Somar Corp.) 06-10-1988.
Biological Abstract, vol. 85, No. 6, 1988, pp. AB-837-838, Abstract No. 60937, Philadelpia, U.S.; Namera et al.

*Primary Examiner*—Elizabeth C. Weimar
*Assistant Examiner*—Che Chereskin
*Attorney, Agent, or Firm*—Sughrue, Mion, Zinn, Macpeak & Seas

[57] ABSTRACT

A method for producing a stigma-like tissue of a saffron flower comprising (1) culturing a corolla tube of a saffron in the presence of a plant hormone or (2) culturing a female organ and/or a corolla tube of a saffron flower in the presence of a plant hormone and alanine, and a method for producing useful components of a saffron flower, e.g., saffron pigment, from the thus produced stigma-like tissue. The tissue cultures produce larger quantitites of the stigma-like tissue and useful components, compared to that obtained by conventional tissue cultures.

10 Claims, 1 Drawing Sheet

METHOD FOR PRODUCING SAFFRON STIGMA-LIKE TISSUE AND METHOD FOR PRODUCING USEFUL COMPONENTS FROM SAFFRON STIGMA-LIKE TISSUE

FIELD OF THE INVENTION

This invention relates to a method for producing a saffron stigma-like tissue in tissue cultures of saffron organs and a method for collecting useful components therefrom, such as pigment.

The present saffron components are useful in the fields of medicine, foodstuffs, and cosmetics, as, for example, sedatives, coloring materials, flavors, and bittering agents.

BACKGROUND OF THE INVENTION

The pistil of the saffron flower is composed of, from the top, a stigma, a style, and an ovary. The stigma has a bright red color and contains useful components including medicinal components, flavoring components and pigments.

The saffron stigmata containing the useful components have been conventionally harvested from the pistils of open saffron flowers. In general, a big saffron bulb weighing about 30g gives rise to only about 6 flowers, each having three-divided stigma. Thus, one can harvest only about 18 stigmata per bulb at the most. In order to collect, for example, 1 kg of stigmata, the required amount of bulbs would amount to about 500 kg. Therefore, the production of large quantities of saffron stigmata requires the cultivation of considerable acreage.

Moreover, natural cultivation is time consuming and subject to weather conditions. Further, saffron is extremely unsuited for repeated cultivation on the same ground. Hence, it is difficult to efficiently produce saffron pitilliary stigmata by cultivation. Thus, saffron stigmata produced under these circumstances, are very expensive.

It has been proposed to culture the organs of the saffron flower to produce a stigma-like tissue, for example, culture the female organ (i.e., pistil) of the saffron flower in the presence of cytokinins and/or orxines to produce a saffron stigma-like tissue (i.e., pistil like tissue) as disclosed in JP-A-62-275617 (the term "JP-A" as used herein means an "unexamined published Japanese patent application"); culture the female organ (i.e., stigma, pistile, ovary or ovule) or a petal of the saffron flower in the presence of cytokinins and orxines as disclosed in JP-A-63-258574. However, a satisfactory technique has not yet been established to obtain sufficient quantities of the saffron stigma-like tissue and the saffron pigment. Thus, there has been a great demand to develop a technique for effectively obtaining saffron useful components.

SUMMARY OF THE INVENTION

An object of this invention is to provide a method for efficiently producing saffron stigma-like tissue containing useful components.

Another object of this invention is to provide a method for efficiently producing useful components of saffron from the thus produced saffron stigma-like tissue.

It has been found that the above objects of this invention can be accomplished by (1) culturing a corolla tube (connate petal) of the saffron flower in tissue culture, or (2) culturing the female organ and/or a corolla tube of the saffron flower in tissue culture in the presence of alanine.

That is, the present invention relates to a method for producing saffron stigma-like tissue, which comprises culturing a corolla tube of a saffron flower in tissue culture to produce a saffron stigma-like tissue.

The present invention further relates to a method for producing saffron stigma-like tissue, which comprises culturing a female organ and/or a corolla tube of a saffron flower in tissue culture in the presence of alanine.

The present invention still further relates to a method for producing useful components of saffron, which comprises recovering saffron useful components from the saffron stigma-like tissue thus produced.

According to the present invention, saffron stigma-like tissue can be efficiently produced, and the saffron useful components can be efficiently collected from the produced stigma-like tissue.

DETAILED DESCRIPTION OF THE INVENTION

Figure 1:
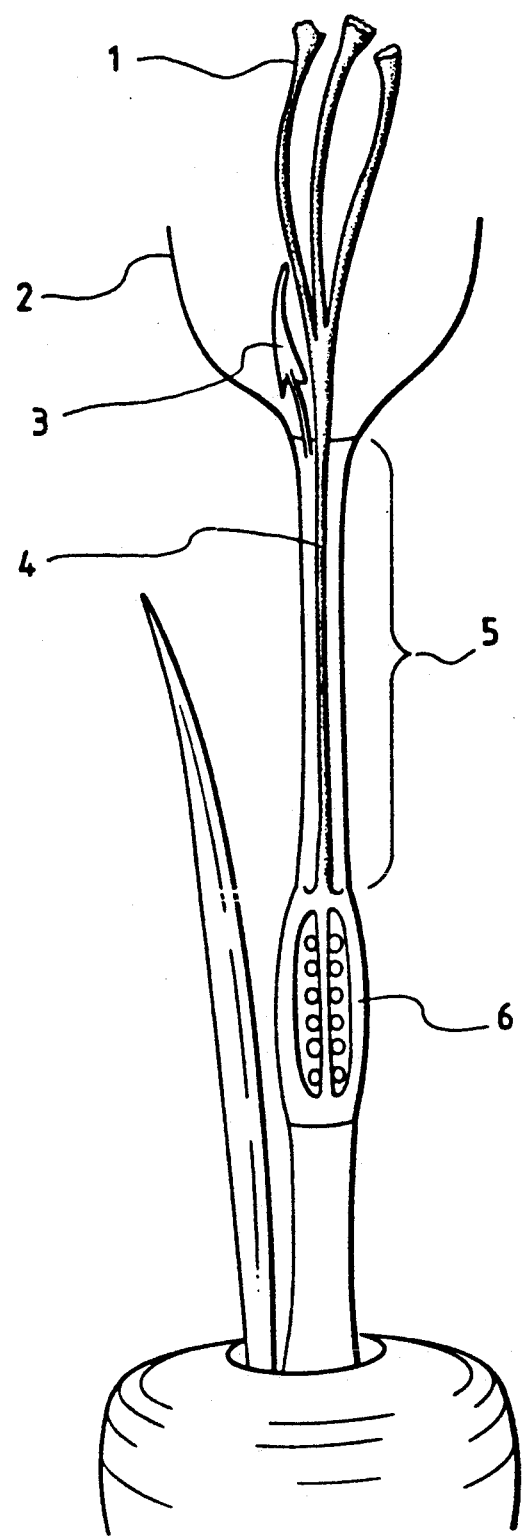
FIG. 1 shows the cross-section of saffron flower. A saffron pistil composed of three parts, i.e., a stigma 1, a style 4, and an ovary 6. A corolla tube 5 is an assembly of petal 2 united into a tubular form, in which a stigma 1, an anther 3, and a style 4 are enveloped.

The term "female organ" as used herein means a pistil composed of three parts, i.e., a stigma, a style, and an ovary. The term "corolla tube" (connate petal) as used herein means an assembly of petals united into a tubular form, in which colored stigmata usually used for medicines or pigment production and a style are enveloped, as defined, for example, in *Saishin Syokubutsu Yogo Jiten*, published by Hirokawa Syoten, page 195.

Useful components of saffron are present in the stigmata constituting a pistil of a saffron flower. The useful components are produced from the stigma-like tissue produced by tissue culture of the organ of a saffron as proposed, for example, in JP-A-62-275617 or JP-A-63-258574. The first embodiment of the present invention is characterized in that the stigma-like tissue is produced in a tissue culture of a corolla tube of a saffron flower, different from the female organ, to produce a larger quantity of the stigma-like tissue easily and thereby to produce a larger quantity of the pigment. In this embodiment, a corolla tube of a saffron flower is tissue-cultured in a medium containing a plant hormone in a bright or dark room to produce and proliferate a colored stigma-like tissue.

Heretofore, it has not been known that tissue culture of a corolla tube of saffron flower, different from the female organ, will produce the useful stigma-like tissue.

In this embodiment, tissue cultures of the female organ of a saffron flower surely produce stigma-like tissue, but the method of using a corolla tube instead of the female organ is superior in terms of volume of the stigma-like tissue produced and volume of the accumulated pigment.

Corolla tubes to be used are harvested from saffron flowers before opening, i.e., flowers in the bud and subjected to tissue culture in the manner as described, for example, in *Syokubutsu Biotechnology*, published by Tokyo Kagaku Dojin, pages 75 to 81 (1986), to produce and proliferate the stigma-like tissue. When using corolla tubes harvested after flower opening, the amount of the stigma-like tissue produced tends to be reduced.

The second embodiment of the present invention is characterized in that a female organ and/or a corolla tube of a saffron flower is tissue-cultured in the presence of alanine to produce and proliferate a colored stigma-like tissue. As compared with the conventional tissue cultures of the female organ, the tissue culture of this embodiment produces a larger quantity of the stigma-like tissue easily and rapidly and thereby a larger quantity of the pigment.

It has been reported that, in the formation of an undifferentiated callus by cultivation of a saffron bulb, the addition of alanine to the medium results in the discharge of a red substance into the medium (*Dai* 10 *Kai Syokubutsu Soshiki Baiyou Symposium Koen Yoshi Syu*, page 147 (1987)). However, heretofore, it has not been known that tissue cultures of a specific organ of saffron in the presence of alanine will produce the useful stigma-like tissue.

In this embodiment, a female organ and/or a corolla tube of a saffron flower is tissue-cultured in a medium containing a plant hormone and alanine in a bright or dark room. This method is far superior to the above-described conventional method in terms of volume of the stigma-like tissue produced and volume of the pigment accumulated.

Female organs and/or corolla tubes to be cultured are harvested from saffron flowers before opening, i.e., flowers in the bud and subjected to tissue culture in the manner as in the first embodiment by using a medium containing alanine to produce and proliferate the stigma-like tissue. When using female organs and/or corolla tubes harvested after flower opening, the amount of the stigma-like tissue produced tends to be reduced.

A typical example of the stigma-like tissue obtained by the present invention is a tissue very similar to a stigma of a saffron pistil in form and has a color changing from yellow to red depending on the amount of the saffron pigment accumulated.

The medium which can be used in each of the first and second embodiments of the present invention is not particularly limited and can be selected from basic media for general plant tissue cultures as described, for example, in *Syokubutsu Saibou Soshiki Baiyou*, published by Rikougakusya, pages 390 to 391 (1979). Suitable culture media include a Murashige-Skoog medium, a White medium, a Linsmaier-Skoog medium, a Gautheret medium, a Tulecke medium, and a Morel medium. A Murashige-Skoog medium and a Linsmaier-Skoog medium are preferred. In the first embodiment, a Murashige-Skoog medium is particularly preferred.

The composition of the typical plant culture medium are indicated in Table 1 below.

TABLE 1

| Composition of Plant Tissue Culture Medium (mg/l) | | | |
| --- | --- | --- | --- |
| Composition | Murashige-Skoog Medium (mg/l) | Linsmaier-Skoog Medium (mg/l) | White Medium (mg/l) |
| (NH4)SO4 | — | — | — |
| MgSO4.7H2O | 370 | 370 | 720 |
| Na2SO4 | — | — | 200 |
| KCl | — | — | 65 |
| CaCl2.2H2O | 440 | 440 | — |
| NaNo3 | — | — | — |
| KNO3 | 1,900 | 1,900 | 80 |
| Ca(NO3)2.4H2O | — | — | 300 |
| NH4NO3 | 1,650 | 1,650 | — |
| NaH2PO4.H2O | — | — | 16.5 |
| NH4H2PO4 | — | — | — |
| KH2PO4 | 170 | 170 | — |
| FeSO4.7H2O | 27.8 | 27.8 | — |
| Na2EDTA | 37.3 | 37.3 | — |
| MnSO4.4H2O | 22.3 | 22.3 | 7 |
| ZnSO4.7H2O | 8.6 | 8.6 | 3 |
| CuSO4.5H2O | 0.025 | 0.025 | — |
| H2SO4 | — | — | — |
| Fe2(SO4)3 | — | — | 2.5 |
| NiCl2.6H2O | — | — | — |
| CoCl2.6H2O | 0.025 | 0.025 | — |
| AlCl3 | — | — | — |
| FeCl3.6H2O | — | — | — |
| FeC6O5H7.5H2O | — | — | — |
| KI | 0.83 | 0.83 | 0.75 |
| H3BO3 | 6.2 | 6.2 | 1.5 |
| Na2MoO4.2H2O | 0.25 | 0.25 | — |
| Sucrose | 30,000 | 30,000 | 20,000 |
| Glucose | — | — | — |
| Myoinositol | 100 | 100 | — |
| Nicotinic Acid | 0.5 | — | 0.5 |
| Pyridoxine Hydrochloride | 0.5 | — | 0.1 |
| Thiamin Hydrochloride | 0.1–1 | 0.4 | 0.1 |
| Calcium Pantothenate | — | — | 1 |
| Biotin | — | — | — |
| Glycine | 2 | — | 3 |
| Cysteine Hydrochloride | — | — | 1 |
| Folic Acid | — | — | — |
| Glutamin | — | — | — |

* Note: in the above Table 1, plant growth regulating substances are not mentioned.

In the first and second embodiments of the present invention, culturing of the female organ or corolla tube is carried out using media containing auxines and cytokinins as plant hormones and, if necessary, alanine.

The auxines to be used in the first and second embodiment of the present invention include α-naphthaleneacetic acid (hereinafter "NAA"), indoleacetic acid, p-chlorophenoxyisobutyric acid, and 2,4-dichlorophenoxyacetic acid, with NAA being preferred. The cytokinins to be used include benzyladenine (hereinafter "BA"), kinetin (hereinafter "Ki"), zeatin, and dihydrozeatin, with BA being preferred.

The auxins are usually added to the medium of the first and second embodiment in concentrations of not less than about 0.1 ppm, preferably from about 0.1 to 10 ppm, more preferably. The cytokinins are usually added in concentrations of not less than 1 ppm, preferably of from about 2 to 15 ppm, more preferably 5 to 15 ppm.

In cases where corolla tubes are cultured in the first embodiment, the culture medium preferably contains sucrose in amounts of not less than 3% by weight, more preferably from about 5 to 12% by weight. If the sucrose concentration is less than about 3%, the production of the stigma-like tissue tends to be lowered. Commonly employed tissue culture media generally has a lower sucrose concentration, i.e., about 3% by weight.

In cases where female organs and/or corolla tubes are cultured in the second embodiment, the culture medium should further contain alanine to accelerate the production of the stigma-like tissue. Alanine is preferably added to a medium in concentrations of from about 0.005 to 10g/l, more preferably from 0.1 to 10g/l. The alanine to be added may be any of D- or L-optical isomers and a racemate.

Tissue culture according to the present invention can be performed either by static culture using a solid medium or by shake culture using a liquid medium. The solid medium includes a medium containing about 0.8% by weight of agar and a Murashige-Skoog medium containing 0.2% by weight of guaran. The culturing may be in either a bright room or a dark room. The culturing temperature is from 15 to 30° C., preferably from 20 to 30° C. When cultured in, for example, a Murashige-Skoog medium at 25° C., stigma-like tissue is produced in 1 to 2 months in the case of culturing the corolla tubes in the first embodiment, or in 4 to 6 weeks in the case of culturing the female organs and/or corolla tubes in the presence of alanine in the second embodiment. The thus produced stigma-like tissue is then subcultured in a solid or liquid medium in a dark or bright room to allow the stigma-like tissue to proliferate.

The saffron pigment in the thus proliferated colored stigma-like tissue can be isolated therefrom by extraction with a solvent, e.g., water, water-containing ethanol, and water-containing propylene glycol, at room temperature or under heating, either as it is obtained from culture or after being ground. Extraction of the saffron pigment, e.g., crocin can be performed by the known method as described, for example, in *Tennentyakusyokuryo Handbook*, published by Korin Syoten, pages 218 to 219 (1979).

For identification, the stigma-like tissue produced by the present invention was extracted with water, and the resulting yellow-colored extract was analyzed by ultraviolet and visible spectrophotometry. When compared with the spectra of an aqueous solution of a naturally-occurring saffron pigment, the pigment obtained by the present invention was confirmed to be equal to the naturally-occurring saffron pigment.

Thus, the present invention makes it possible to obtain large quantities of saffron pigment in a reduced period of time without depending on the weather or season as compared with the natural cultivation of a saffron plant. The stigma-like tissue obtained in the present invention and the pigment extracted therefrom are effectively useful as coloring materials for foodstuffs or cosmetics or raw materials for medicines.

The present invention is now illustrated in greater detail by way of the following Examples and Comparative Examples, but the present invention is not deemed to be limited thereto.

EXAMPLE 1

A BA and NAA were added to a Murashige-Skoog medium (hereinafter "MS medium") in the concentrations shown in Table 2, and the sucrose concentration was adjusted as shown in Table 2. Guaran powder was added to the medium in a concentration of 0.2% by weight, and the medium was sterilized at 120° C. for 20 minutes in an autoclave. The sterilized medium was aloguated into sterile plastic plates having a diameter of 55 mm, followed by cooling to solidify.

A bud of a saffron flower before opening was harvested, and sterilized by soaking in a 0.5 vol% sodium hypochlorite aqueous solution for 10 minutes, and washed with water. The corolla tube portion of the bud was taken out and cut to pieces of about 5 mm. Each cut piece was seeded on each of the above-prepared plates of solid media.

The corolla tube was subjected to static culture at 25° C. in a dark room. Production of a stigma-like tissue was recognized in the cultures in about 6 weeks at the soonest. In 8 weeks, the stigma-like tissue grew and assumed a red color, indicating considerable production of the saffron pigment.

After 8 weeks' culturing, the tissue cultures were visually observed to determine the amount and the color density of the stigma-like tissue containing the saffron pigment which was produced per explant (piece of the corolla tube) and evaluated according to the following scales. The results obtained are shown in Tables 2 and 3.

Scale of Evaluation

The relative amount of the stigma-like tissue was visually determined and rated according to an 11-part divided scale, taking an amount corresponding to the amount of naturally-occurring three stigmata containing saffron pigment as 10, nil as 0, and equally dividing the interval therebetween.

The relative color density of the stigma-like tissue was visually determined, and rated according to an 11-part divided scale, taking a density corresponding to the density of a naturally-occurring stigma containing saffron pigment as 10 and colorlessness as 0, and equally dividing the interval therebetween.

TABLE 2

Relative Production of Stigma-Like Tissue Containing Saffron Pigment

| BA (ppm) | NAA (ppm) | Sucrose Concentration (wt %) | | | | | | |
|---|---|---|---|---|---|---|---|---|
| | | 2 | 3 | 5 | 6 | 9 | 12 | 15 |
| 10 | 0.05 | 3 | 3 | 4 | 4 | 4 | 4 | 3 |
| 10 | 0.1 | 3 | 4 | 5 | 5 | 6 | 6 | 4 |
| 10 | 1 | 3 | 5 | 6 | 6 | 6 | 6 | 5 |
| 10 | 10 | 3 | 4 | 5 | 5 | 6 | 6 | 5 |
| 10 | 15 | 3 | 3 | 4 | 4 | 4 | 4 | 4 |

TABLE 3

Relative Color Density of Stigma-Like Tissue Containing Saffron Pigment

| BA (ppm) | NAA (ppm) | Sucrose Concentration (wt %) | | | | | | |
|---|---|---|---|---|---|---|---|---|
| | | 2 | 3 | 5 | 6 | 9 | 12 | 15 |
| 10 | 0.05 | 7 | 7 | 7 | 7 | 8 | 8 | 7 |
| 10 | 0.1 | 7 | 8 | 9 | 9 | 9 | 9 | 8 |
| 10 | 1 | 7 | 8 | 9 | 9 | 9 | 9 | 8 |
| 10 | 10 | 8 | 8 | 8 | 9 | 9 | 9 | 7 |
| 10 | 15 | 7 | 7 | 8 | 7 | 8 | 8 | 7 |

COMPARATIVE EXAMPLE 1

Tissue culturing was conducted in the same manner as in Example 1, except for replacing the corolla tube with the ovary taken from the same bud as used in Example 1. The results obtained are shown in Tables 4 and 5.

TABLE 4

Relative Production of Stigma-Like Tissue Containing Saffron Pigment

| BA (ppm) | NAA (ppm) | Sucrose Concentration (wt %) | | |
|---|---|---|---|---|
| | | 3 | 6 | 9 |
| 10 | 0.1 | 3 | 3 | 4 |
| 10 | 1 | 3 | 3 | 4 |

TABLE 4-continued

Relative Production of Stigma-Like
Tissue Containing Saffron Pigment

| BA (ppm) | NAA (ppm) | Sucrose Concentration (wt %) | | |
|---|---|---|---|---|
| | | 3 | 6 | 9 |
| 10 | 10 | 3 | 3 | 3 |

TABLE 5

Relative Color Density of Stigma-Like
Tissue Containing Saffron Pigment

| BA (ppm) | NAA (ppm) | Sucrose Concentration (wt %) | | |
|---|---|---|---|---|
| | | 3 | 6 | 9 |
| 10 | 0.1 | 7 | 8 | 8 |
| 10 | 1 | 8 | 7 | 8 |
| 10 | 10 | 7 | 7 | 7 |

EXAMPLE 2

Tissue culturing was conducted in the same manner as in Example 1, except for replacing the MS medium as used in Example 1 with a modified MS medium (MS-1 or MS-2) having the same composition as the MS medium but with its concentrations of inorganic salts being altered as shown in Table 6, and fixing the sucrose concentration at 6% by weight. The resulting cultures were evaluated in the same manner as in Example 1, and the results obtained are shown in Tables 7 and 8.

As can be seen from tables 7 and 8, satisfactory results similarly to Example 1 were obtained.

TABLE 6

| | MS Medium (mg/l) | MS Modified Medium* | |
|---|---|---|---|
| | | MS-1 (mg/l) | MS-2 (mg/l) |
| $NH_4NO_3$ | 1650 | 825 | |
| $KNO_3$ | 1900 | 950 | |
| $KH_2PO_4$ | 170 | 85 | |
| $H_3BO_3$ | 6.2 | | 3.1 |
| $MnSO_4.4H_2O$ | 22.3 | | 11.15 |
| $ZnSO_4.4H_2O$ | 8.6 | | 4.3 |
| KI | 0.83 | | 0.415 |
| $Na_2MoO_4.2H_2O$ | 0.25 | | 0.125 |
| $CuSO_4.5H_2O$ | 0.025 | | 0.0125 |
| $CoCl_2.6H_2O$ | 0.025 | | 0.0125 |

Note: Only the alterations from the MS medium are shown.

TABLE 7

Relative Production of Stigma-Like
Tissue Containing Saffron Pigment

| BA (ppm) | NAA (ppm) | MS Modified Medium | |
|---|---|---|---|
| | | MS-1 | MS-2 |
| 10 | 0.1 | 5 | 5 |
| 10 | 1 | 5 | 5 |

TABLE 8

Relative Color Density of Stigma-Like
Tissue Containing Saffron Pigment

| BA (ppm) | NAA (ppm) | MS Modified Medium | |
|---|---|---|---|
| | | MS-1 | MS-2 |
| 10 | 0.1 | 8 | 8 |
| 10 | 1 | 9 | 9 |

It can be seen from Examples 1 and 2 in view of Comparative Example 1 that the tissue culturing of corolla tubes produces satisfactory amounts of the stigma-like tissue and the pigment.

EXAMPLE 3

To an MS medium were added, BA, NAA and alanine in concentrations shown in Table 9. Guaran powder was then added to the medium in a concentration of 0.2% by weight. The medium was sterilized at 120° C. for 20 minutes in an autoclave. The sterilized medium was aloquated into sterile plastic plates having a diameter of 55 mm, followed by cooling to solidify.

A bud of a saffron flower before opening was harvested, sterilized by soaking in a 0.5 vol% sodium hypochlorite aqueous solution for 10 minutes, and washed with water. The ovary portion of the bud was taken out and cut to pieces of about 8 mm. Each cut piece was seeded on each of the above-prepared solid media.

The ovary was subjected to static culture at 25° C. in a dark room. Production of a stigma-like tissue was recognized in the cultures in about 4 weeks at the soonest. In 7 weeks, the stigma-like tissue grew and assumed a red color, indicating considerable production of the saffron pigment.

After 7 weeks of culturing, the tissue cultures were visually observed and evaluated in the same manner as in Example 1. The results obtained are shown in Tables 9 and 10.

COMPARATIVE EXAMPLE 2

A saffron ovary was cultured in the same manner as in Example 3, except that alanine was not added to the medium. The results obtained are shown in Tables 9 and 10.

TABLE 9

Relative Production of Stigma-Like
Tissue Containing Saffron Pigment

| BA (ppm) | NAA (ppm) | Alanine Concentration (g/l) | | | | | | | |
|---|---|---|---|---|---|---|---|---|---|
| | | 0.005 | 0.01 | 0.1 | 1.0 | 5.0 | 10.0 | 20.0 | 0 |
| 10 | 0.1 | 4 | 5 | 5 | 7 | 6 | 5 | 3 | 3 |
| 10 | 1.0 | 4 | 5 | 6 | 8 | 6 | 5 | 4 | 3 |

TABLE 10

Relative Color Density of Stigma-Like
Tissue Containing Saffron Pigment

| BA (ppm) | NAA (ppm) | Alanine Concentration (g/l) | | | | | | | |
|---|---|---|---|---|---|---|---|---|---|
| | | 0.005 | 0.01 | 0.1 | 1.0 | 5.0 | 10.0 | 20.0 | 0 |
| 10 | 0.1 | 8 | 8 | 9 | 9 | 9 | 8 | 8 | 7 |
| 10 | 1.0 | 8 | 8 | 9 | 9 | 8 | 8 | 7 | 8 |

EXAMPLE 4

A saffron ovary was cultured in the same manner as in Example 3, except for replacing the MS medium with a Linsmaier-Skoog medium to which Ki, NAA and alanine were added in the concentrations shown in Table 11. The results obtained are shown in Tables 11 and 12.

COMPARATIVE EXAMPLE 3

A saffron ovary was cultured in the same manner as in Example 4, except that alanine was not added to the medium. The results obtained are shown in Tables 11 and 12.

TABLE 11

Relative Production of Stigma-Like Tissue Containing Saffron Pigment

| Ki (ppm) | NAA (ppm) | Alanine Concentration (g/l) | | | | |
|---|---|---|---|---|---|---|
| | | 0.01 | 0.1 | 1.0 | 5.0 | 0 |
| 2 | 0.1 | 3 | 4 | 5 | 5 | 1 |
| 2 | 1.0 | 3 | 4 | 5 | 5 | 2 |

TABLE 12

Relative Color Density of Stigma-Like Tissue Containing Saffron Pigment

| Ki (ppm) | NAA (ppm) | Alanine Concentration (g/l) | | | | |
|---|---|---|---|---|---|---|
| | | 0.01 | 0.1 | 1.0 | 5.0 | 0 |
| 2 | 0.1 | 5 | 6 | 7 | 6 | 3 |
| 2 | 1.0 | 6 | 6 | 7 | 7 | 3 |

EXAMPLE 5

The procedure of Example 4 was repeated except for replacing the ovary with a corolla tube of a saffron. The results obtained are shown in Tables 13 and 14.

COMPARATIVE EXAMPLE 4

The corolla tube was cultured in the same manner as in Example 4, except that alanine was not added to the medium. The results obtained are shown in Tables 13 and 14.

TABLE 13

Relative Production of Stigma-Like Tissue Containing Saffron Pigment

| Ki (ppm) | NAA (ppm) | Alanine Concentration (g/l) | | | | |
|---|---|---|---|---|---|---|
| | | 0.01 | 0.1 | 1.0 | 5.0 | 0 |
| 2 | 0.1 | 4 | 5 | 6 | 6 | 2 |
| 2 | 1.0 | 4 | 5 | 6 | 6 | 3 |

TABLE 14

Relative Color Density of Stigma-Like Tissue Containing Saffron Pigment

| Ki (ppm) | NAA (ppm) | Alanine Concentration (g/l) | | | | |
|---|---|---|---|---|---|---|
| | | 0.01 | 0.1 | 1.0 | 5.0 | 0 |
| 2 | 0.1 | 6 | 7 | 7 | 7 | 3 |
| 2 | 1.0 | 6 | 7 | 7 | 7 | 4 |

From the foregoing results, it is apparent that tissue cultures of the female organ and/or corolla tube of saffron in the presence of alanine produce larger quantities of stigma-like tissue and the pigment as compared with those in the absence of alanine.

EXAMPLE 6

The procedure of Example 4 was repeated except for replacing the overy with a style of saffron. The results obtained are shown in Tables 15 and 16.

COMPARATIVE EXAMPLE 5

The style was cultured in the same manner as in Example 4, except that alanine was not added to the medium. The results obtained are shown in Table 15 and 16.

TABLE 15

Relative Production of Stigma-Like Tissue Containing Saffron Pigment

| Ki (ppm) | NAA (ppm) | Alanine Concentration (g/l) | | | |
|---|---|---|---|---|---|
| | | 0.1 | 1.0 | 5.0 | 0 |
| 2 | 0.1 | 4 | 5 | 5 | 2 |
| 2 | 1.0 | 5 | 6 | 6 | 2 |

TABLE 16

Relative Density of Stigma-Like Tissue Containing Saffron Pigment

| Ki (ppm) | NAA (ppm) | Alanine Concentration (g/l) | | | |
|---|---|---|---|---|---|
| | | 0.1 | 1.0 | 5.0 | 0 |
| 2 | 0.1 | 6 | 7 | 7 | 3 |
| 2 | 1.0 | 7 | 7 | 8 | 3 |

EXAMPLE 7

The procedure of Example 4 was repeated except for replacing the ovary with a stigma of saffran. The results obtained are shown in Tables 17 and 18.

COMPARATIVE EXAMPLE 6

The stigma was cultured in the same manner as in Example 7, except that alanine was not added to the medium. The results obtained are shown in Tables 17 and 18.

TABLE 17

Relative Production of Stigma-Like Tissue Containing Saffron Pigment

| Ki (ppm) | NAA (ppm) | Alanine Concentration (g/l) | | | |
|---|---|---|---|---|---|
| | | 0.1 | 1.0 | 5.0 | 0 |
| 2 | 0.1 | 3 | 4 | 4 | 1 |
| 2 | 1.0 | 4 | 4 | 4 | 1 |

TABLE 18

Relative Color Density of Stigma-Like Tissue Containing Saffron Pigment

| Ki (ppm) | NAA (ppm) | Alanine Concentration (g/l) | | | |
|---|---|---|---|---|---|
| | | 0.1 | 1.0 | 5.0 | 0 |
| 2 | 0.1 | 6 | 8 | 7 | 3 |
| 2 | 1.0 | 8 | 8 | 7 | 4 |

While the invention has been described in detail and with reference to specific embodiments thereof, it will be apparent to one skilled in the art that various changes and modifications can be made therein without departing from the spirit and scope thereof.

What is claimed is:

1. A method for producing stigma-like tissue from a saffron flower, comprising the step of:
    culturing a corolla tube of a saffron flower by tissue culture in a medium containing at least an auxin, a cytokinin and sucrose, wherein said auxin is present in a concentration of not less than 0.1 ppm, said cytokinin is present in a concentration of not less than 1.0 ppm, and sucrose is present in an amount of 5 to 12 wt % for a time sufficient for the development of stigma-like tissue.

2. The method as claimed in claim 1, wherein said auxin is present in a concentration of from 0.1 to 10 ppm and said cytokinin is present in a concentration of from 2 to 15 ppm.

3. The method as claimed in claim 1, wherein said auxin is α-naphthaleneacetic acid and said cytokinin is benzyladenine.

4. A method for producing stigma-like tissue from a saffron flower comprising the step of:

culturing a corolla tube of a saffron flower by tissue culture in a medium containing at least an auxin, a cytokinin and alanine, wherein said auxin is present in a concentration of not less than 0.1 ppm and said cytokinin is present in a concentration of not less that 1.0 ppm for a time sufficient for the development of stigma-like tissue.

5. The method as claimed in claim 4, wherein said alanine is employed in an amount of from 0.005 to 10g/l.

6. The method as claimed in claim 4, wherein said alanine is employed in an amount of from 0.1 to 10g/l.

7. The method as claimed in claim 4, wherein said auxin is present in a concentration of from 0.1 to 10 ppm and said cytokinin is present in a concentration of from 2 to 15 ppm.

8. The method as claimed in claim 4, wherein said auxin is α-naphthaleneacetic acid and said cytokinin is benzyladenine or kinetin.

9. A method for producing saffron pigment of a saffron flower, comprising the steps of:

(A) culturing a corolla tube of a saffron flower by tissue culture in a medium containing, an auxin, a cytokinin and sucrose, wherein said auxin is present in a concentration of not less than 0.1 ppm, said cytokinin is present in a concentration of not less than 1.0 ppm, and sucrose is present in an amount of 5 to 12 wt % to produce stigma tissue; and (B) isolating the saffron pigment from the resulting stigma tissue of step (A).

10. A method for producing useful components of a saffron flower, comprising the steps of:

(A) culturing a corolla tube of a saffron flower by tissue culture in a medium containing an auxin, a cytokinin, and alanine, wherein said auxin is present in a concentration of not less than 0.1 ppm and said cytokinin is present in a concentration of not less than 1.0 ppm, to produce stigma tissue; and (B) isolating the saffron pigment from the resulting stigma tissue of step (A).

* * * * *